United States Patent
Fong

(10) Patent No.: US 7,949,388 B1
(45) Date of Patent: May 24, 2011

(54) METHODS AND SYSTEMS TO CHARACTERIZE ST SEGMENT VARIATION OVER TIME

(75) Inventor: Jon Jody Fong, Calabasas, CA (US)

(73) Assignee: Pacesetter, Inc., Sylmar, CA (US)

(*) Notice: Subject to any disclaimer, the term of this patent is extended or adjusted under 35 U.S.C. 154(b) by 689 days.

(21) Appl. No.: 11/687,542

(22) Filed: Mar. 16, 2007

(51) Int. Cl.
*A61B 5/04* (2006.01)

(52) U.S. Cl. .................................................. 600/509

(58) Field of Classification Search .............. 600/509, 600/513–517
See application file for complete search history.

(56) References Cited

U.S. PATENT DOCUMENTS

| | | |
|---|---|---|
| 4,531,527 A | 7/1985 | Reinhold, Jr. et al. |
| 4,974,162 A | 11/1990 | Siegel et al. |
| 4,989,610 A | 2/1991 | Patton et al. |
| 5,113,869 A | 5/1992 | Nappholz et al. |
| 5,135,004 A | 8/1992 | Adams et al. |
| 5,199,428 A | 4/1993 | Obel et al. |
| 5,203,326 A | 4/1993 | Collins |
| 5,251,621 A | 10/1993 | Collins |
| 5,313,953 A | 5/1994 | Yomtov et al. |
| 5,388,578 A | 2/1995 | Yomtov et al. |
| 5,410,473 A | 4/1995 | Kaneko et al. |
| 5,497,780 A | 3/1996 | Zehender |
| 5,531,768 A | 7/1996 | Alferness |
| 5,891,047 A * | 4/1999 | Lander et al. ................ 600/516 |
| 6,016,443 A | 1/2000 | Ekwall et al. |
| 6,021,350 A | 2/2000 | Mathson |
| 6,108,577 A | 8/2000 | Benser |
| 6,112,116 A | 8/2000 | Fischell et al. |
| 6,115,628 A | 9/2000 | Stadler et al. |
| 6,128,526 A | 10/2000 | Stadler et al. |
| 6,233,486 B1 | 5/2001 | Ekwall et al. |
| 6,256,538 B1 | 7/2001 | Ekwall |
| 6,264,606 B1 | 7/2001 | Ekwall et al. |
| 6,272,379 B1 | 8/2001 | Fischell et al. |
| 6,324,421 B1 | 11/2001 | Stadler et al. |
| 6,368,284 B1 | 4/2002 | Bardy |
| 6,381,493 B1 | 4/2002 | Stadler et al. |
| 6,468,263 B1 | 10/2002 | Fischell et al. |
| 6,501,983 B1 | 12/2002 | Natarajan et al. |
| 6,609,023 B1 | 8/2003 | Fischell et al. |
| 6,937,899 B2 | 8/2005 | Sheldon et al. |
| 2002/0143262 A1 | 10/2002 | Bardy |
| 2002/0143263 A1 | 10/2002 | Shusterman |
| 2004/0260188 A1 | 12/2004 | Syed et al. |

(Continued)

FOREIGN PATENT DOCUMENTS

EP 0839544 B1 7/2003

(Continued)

OTHER PUBLICATIONS

NonFinal Office Action, mailed Nov. 20, 2009: Related U.S. Appl. No. 11/833,139.

(Continued)

*Primary Examiner* — Mark W Bockelman
*Assistant Examiner* — Elizabeth K So

(57) ABSTRACT

A system and method are provided for characterizing ST segment (STS) variations of a patient. The method includes collecting STS variations for multiple data collection periods, calculating multiple statistical parameters based on the collected STS variations, and constructing a STS variation trend. The statistical parameters are associated with a corresponding data collection period. The STS variation trend is based on the multiple statistical parameters over multiple data collection periods.

18 Claims, 14 Drawing Sheets

U.S. PATENT DOCUMENTS

| | | |
|---|---|---|
| 2005/0059897 A1 | 3/2005 | Snell et al. |
| 2005/0113705 A1 | 5/2005 | Fischell et al. |
| 2005/0256417 A1 | 11/2005 | Fischell et al. |
| 2006/0009811 A1 | 1/2006 | Sheldon et al. |
| 2006/0116593 A1 | 6/2006 | Zhang et al. |
| 2006/0265020 A1 | 11/2006 | Fischell et al. |
| 2007/0208263 A1 | 9/2007 | John et al. |

FOREIGN PATENT DOCUMENTS

| | | |
|---|---|---|
| EP | 1164933 B1 | 5/2006 |
| WO | 0057781 | 10/2000 |
| WO | WO 03/020366 A1 | 3/2003 |
| WO | WO 03/020367 A1 | 3/2003 |
| WO | WO 2004/047917 A1 | 6/2004 |

OTHER PUBLICATIONS

NonFinal Office Action, mailed Jun. 24, 2009: Related U.S. Appl. No. 11/735,254.

Final Office Action, mailed Jun. 24, 2009: Related U.S. Appl. No. 11/735,254.

Final Office Action, mailed May 4, 2010: Related U.S. Appl. No. 11/833,139.

Advisory Action, mailed Jun. 28, 2010: Related U.S. Appl. No. 11/833,139.

\* cited by examiner

METHODS AND SYSTEMS TO CHARACTERIZE ST SEGMENT VARIATION OVER TIME

RELATED APPLICATIONS

This application is related to the following U.S. Patent Applications:
1) Ser. No. 11/833,139, filed Aug. 2, 2007, "Stress Test for Analyzing Coronary Burden Utilizing ST Segment Variation,"; and
2) Ser. No. 11/735,254, filed Apr. 13, 2007, "Ischemia Detection Methods and Systems Adaptive to Changes in ST Segment Shift,".

BACKGROUND OF THE INVENTION

Embodiments of the present invention pertain generally to implantable medical devices, and more particularly pertain to medical devices that utilize STS segment variations within cardiac signals to characterize a patient's myocardial condition.

Cardiac ischemia is a condition whereby heart tissue does not receive adequate amounts of oxygen and is usually caused by a blockage of an artery leading to heart tissue. Ischemia arises during angina, acute myocardial infarction, coronary angioplasty, and any other condition that compromises blood flow to a region of tissue. When blockage of an artery is sufficiently severe, the cardiac ischemia becomes an acute myocardial infarction (AMI), also referred to as a myocardial infarction (MI) or a heart attack.

Many patients at risk of cardiac ischemia have pacemakers, implantable cardioverter/defibrillators (ISCDs) or other medical devices implanted therein. Cardiac signals can be characterized by electrocardiograms (ECG) and/or intra-cardiac electrograms (IEGM). ECGs and IEGMs are useful for diagnosing ischemia and locating damaged areas within the heart. ECGs are composed are various waves and segments that represent the heart depolarizing and repolarizing. The ST segment (STS) represents the portion of the cardiac signal between ventricular depolarization and ventricular repolarization. While P-waves, R-waves and T-waves may be generally considered features of a surface electrocardiogram (ECG), for convenience and generality, herein the terms R-wave, T-wave and P-wave are also used to refer to the corresponding internal cardiac signal, such as an intra-cardiac electrogram (IEGM).

Techniques have been developed for detecting cardiac ischemia using implanted medical devices. Some conventional IEGM-based ischemia detection techniques seek to detect ischemia by identifying changes in the elevation and/or depression of the STS from the baseline of the cardiac signal that occur during cardiac ischemia. Elevation and/or depression of the STS in a cardiac signal may result when there are abnormalities in the polarizations of cardiac tissue during an acute myocardial infraction (MI). An STS variation arises because of differences in the electric potential between cells that have become ischemic and those cells that are still receiving normal blood flow. Variation of the STS from a baseline is a result of injury to cardiac muscle, changes in the synchronization of ventricular muscle depolarization, drug or electrolyte influences, or the like.

Patients that experience ischemia events may show signs of STS elevation or depression. Conventionally, STS variations found in cardiac signals are captured and displayed in a limited manner. However the conventional presentation of STS variation has provided limited information. For instance, conventional presentation formats show STS variation for near term events (e.g., one to seven days) which are not sufficient indicators of ischemia that develops more slowly over longer periods of time. Thus, conventional presentation formats for STS variation can mask ischemia that develops over a longer period of time. Therefore, a reliable presentation and ischemia detection method and system are needed that are able to measure the STS variation trend over a long period of time and present the trend in a manner that more readily indicates potential changes in ischemia events.

SUMMARY

In accordance with at least one embodiment, a method is provided for characterizing STS variations of a patient. The method includes collecting STS variations for multiple data collection periods, calculating multiple statistical parameters based on the collected STS variations, and constructing a STS variation trend. The statistical parameters are associated with a corresponding data collection period. The STS variation trend is based on the multiple statistical parameters over multiple data collection periods.

In accordance with another embodiment, a system for characterizing ST segment (STS) variations of a patient is provided. The system includes a memory module and a processor module. The memory module stores a plurality of cardiac signals having ST segments collected during multiple data collection periods, where each of the data collection periods is separated by a cycle. In addition, the memory module stores the values of STS variations. The processor module is configured to calculate multiple statistical parameters based on the STS variations recorded by the memory module and to construct a STS variation trend based on the statistical parameters.

In accordance with another embodiment, a computer readable medium for use in a medical device having a memory and a programmable microcontroller is provided. The computer readable medium includes instructions to direct the memory to collect and store STS variations and heart rates associated with each STS variation for multiple data collection periods. Instructions also direct the microcontroller to calculate multiple statistical parameters based on the STS variations and to construct a STS variation trend based on the multiple statistical parameters over multiple data collection periods.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

Figure 1:
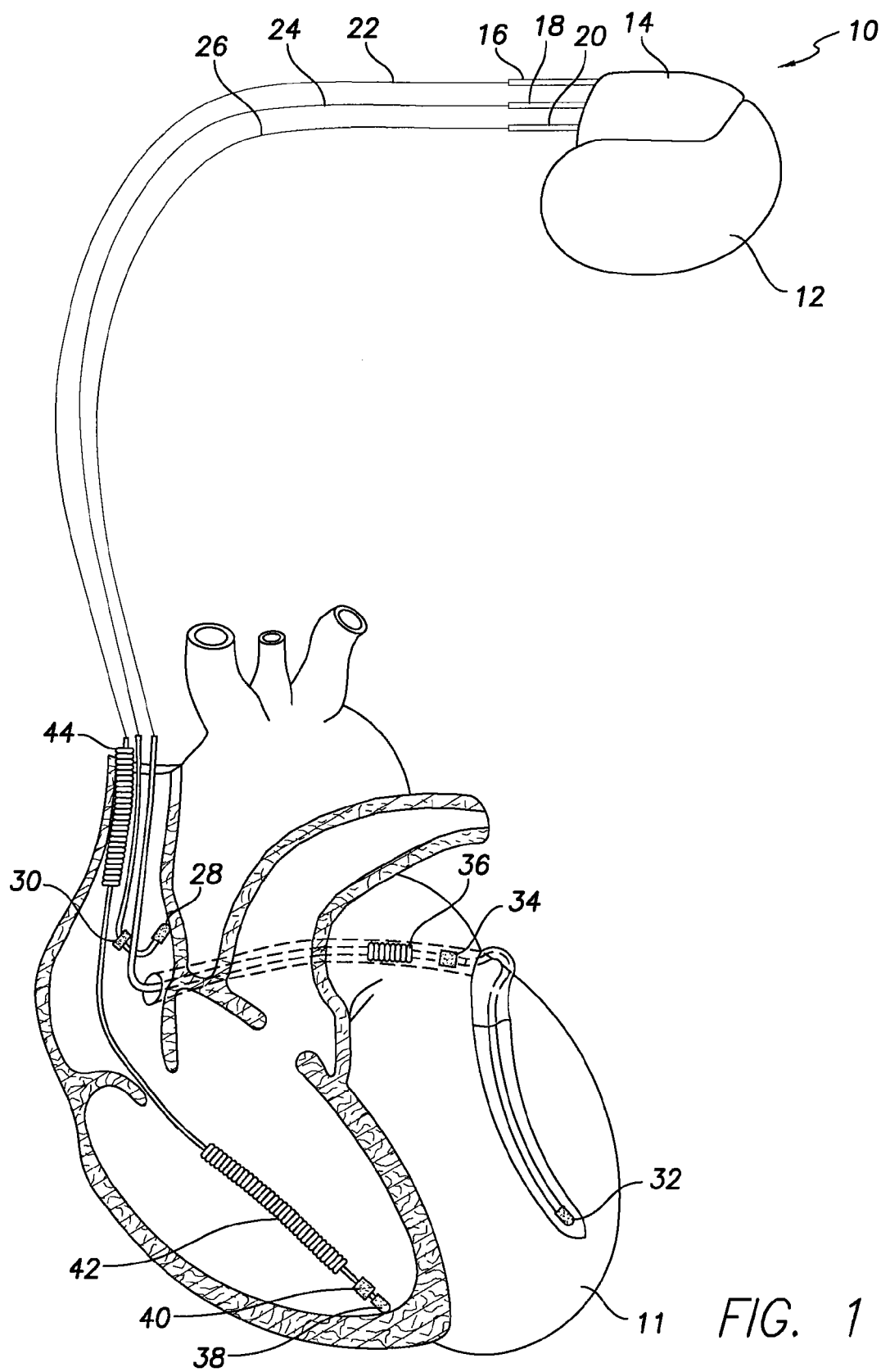
FIG. 1 illustrates an implantable medical device formed in accordance with an embodiment of the present invention.

FIG. 1 illustrates an implantable medical device 10 (IMD) that is coupled to a heart 11. The implantable medical device 10 may be a cardiac pacemaker, an implantable cardioverter defibrillator (ICD), a defibrillator, implantable cardioverter/defibrillators (ISCDs), or an ICD coupled with a pacemaker implemented in accordance with an embodiment of the present invention. The IMD 10 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. As explained below in more detail, the IMD 10 may be controlled to monitor cardiac signals and, to identify potentially abnormal physiology (e.g., ischemic).

The IMD 10 includes a housing 12 that is joined to a header assembly 14 (e.g., an IS-4 connector assembly) that holds receptacle connectors 16, 18, and 20 that are connected to a right ventricular lead 22, a right atrial lead 24, and a coronary sinus lead 26, respectively. The leads 22, 24 and 26 may be located at various locations, such as an atrium, a ventricle, or both to measure the physiological condition of the heart 11.

One or more of the leads 22, 24 and 26 detect cardiac signals that form an electrical activity indicator of myocardial function over multiple cardiac cycles. To sense atrial cardiac signals and to provide right atrial chamber stimulation therapy, the right atrial lead 24 having at least an atrial tip electrode 28, which is typically implanted in the right atrial appendage, and an atrial ring electrode 30. The cardiac signals represent analog signals that are subsequently digitized and analyzed to identify waveforms of interest. Examples of waveforms identified from the cardiac signals include the P-wave, T-wave, the R-wave, the QRS complex and the like that are used to describe, for example, electrocardiograms (ECGs) and intracardiac electrograms (IEGMs). The waveforms of interest may be collected over a period of time.

The coronary sinus lead 26 receives atrial and ventricular cardiac signals and delivers left ventricular pacing therapy using at least a left ventricular tip electrode 32, left atrial pacing therapy using at least a left atrial ring electrode 34, and shocking therapy using at least a left atrial coil electrode 36. The right ventricular lead 22 has a right ventricular tip electrode 38, a right ventricular ring electrode 40, a right ventricular (RV) coil electrode 42, and a SVC coil electrode 44. Therefore, the right ventricular lead 22 is capable of receiving cardiac signals and delivering stimulation in the form of pacing and shock therapy to the right ventricle.

Figure 2A:
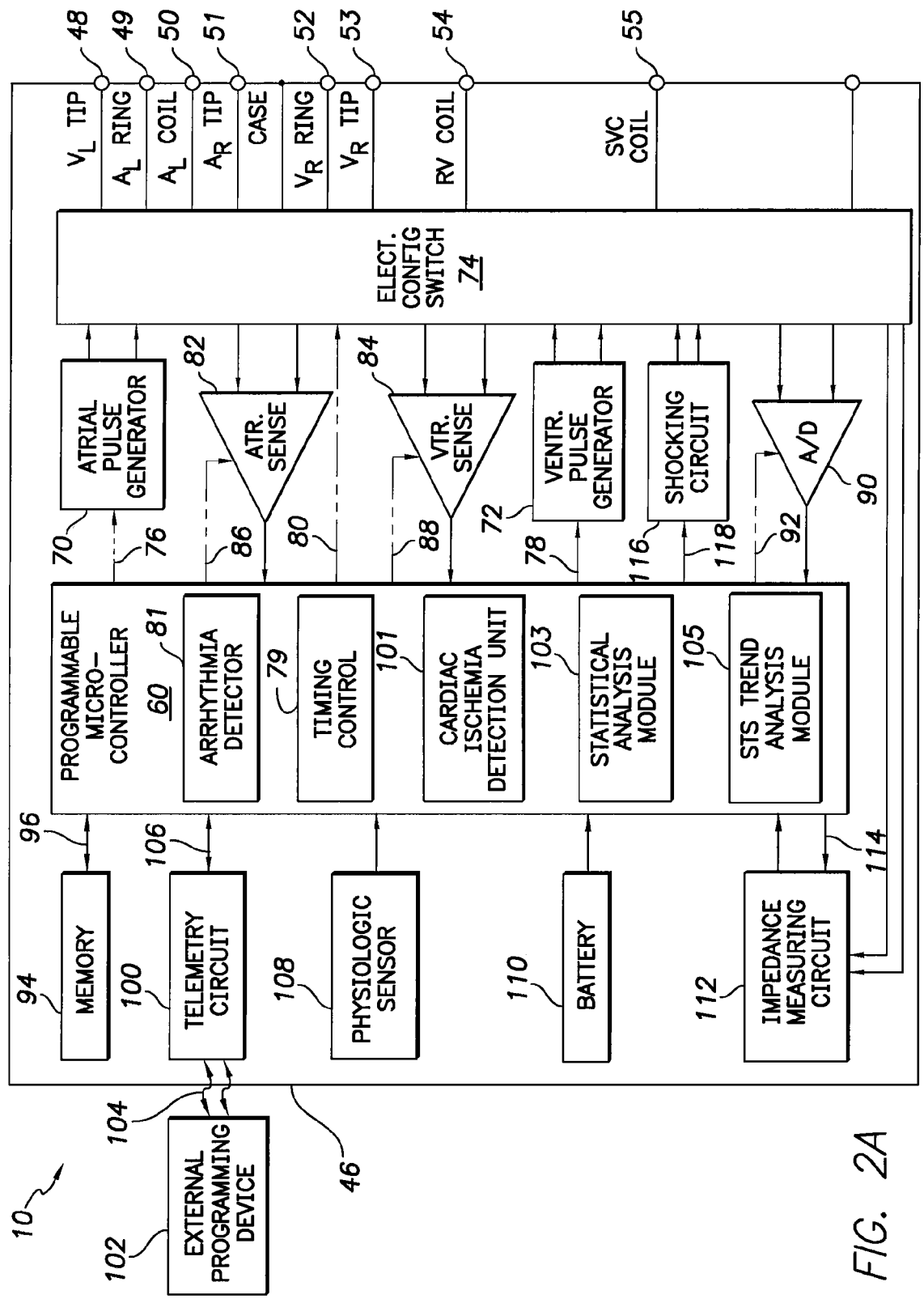
FIGS. 2A and 2B illustrate a functional block diagram of exemplary internal components of an implantable medical device formed in accordance with an embodiment of the present invention.
Figure 2B:
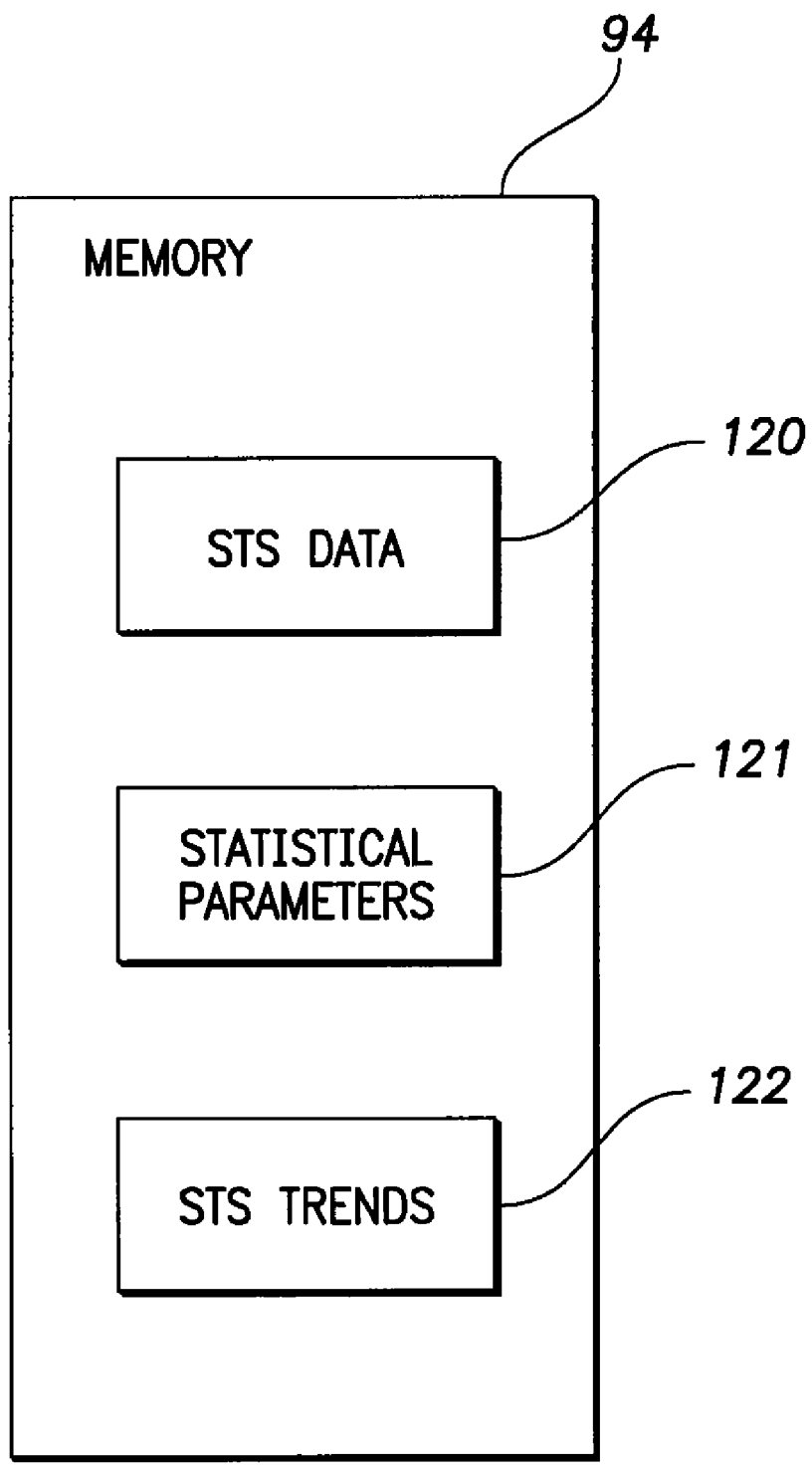

FIGS. 2A and 2B illustrate a block diagram of exemplary internal components of the IMD 10. The IMD 10 is for illustration purposes only, and it is understood that the circuitry could be duplicated, eliminated or disabled in any desired combination to provide a device capable of treating the appropriate chamber(s) of the heart with cardioversion, defibrillation, and/or pacing stimulation.

The housing 46 for IMD 10 (shown schematically in FIG. 2A), is often referred to as the "can", "case" or "case electrode" and may be programmably selected to act as the return electrode for all "unipolar" modes. The housing 46 further includes a connector (not shown) having a plurality of terminals, namely a right atrial tip terminal ($A_R$ TIP) 51, a left ventricular tip terminal ($V_L$ TIP) 48, a left atrial ring terminal ($A_L$ RING) 49, a left atrial shocking terminal ($A_L$ COIL) 50, a right ventricular tip terminal ($V_R$ TIP) 53, a right ventricular ring terminal ($V_R$ RING) 52, a right ventricular shocking terminal (RV COIL) 54, and an SVC shocking terminal (SVC COIL) 55.

The IMD 10 includes a programmable microcontroller 60, which controls the operation of the IMD 10 based on acquired cardiac signals. The IMD 10 may collect the cardiac signals (e.g., ST segment variations) and transmit the cardiac signals to a remove device without any subsequent analysis of the cardiac data. Optionally, IMD 10 may collect the cardiac signals and process the cardiac signals (e.g., determine a statistical parameter and STS trends), and transmit the cardiac signals and the statistical parameters and STS trends. Alternatively, IMD 10 may calculate the statistical parameters but not calculate any STS trends, and transmit the statistical parameters to a remote site. In one example, IMD 10 has the microcontroller 60 to monitor the cardiac signals to identify therein ST segment variations and determine a potential ischemic condition. A cardiac ischemia detection unit 101 controls the detection of episodes of cardiac ischemia. The microcontroller 60 (also referred to herein as a processor module or unit) typically includes a microprocessor, or equivalent control circuitry, is designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in memory. Among other things, the microcontroller 60 receives, processes, and manages storage of digitized data from the various electrodes.

The microcontroller 60 may also analyze the data, for example, in connection with collecting, over a period of time, reference STS variations in a cardiac signal (e.g., sense signals received from leads 22, 24 and 26). The microcontroller 60 may also measure STS variations and compare them to the STS threshold to identify a potential abnormal physiology (e.g., such as when the patient is having a post-myocardial infarct, a "silent" myocardial infarct, a myocardial infarct, an ischemia, a heart block, an arrhythmia, fibrillation, congestive heart failure, and the like). A statistical analysis module 103 examines the raw STS variation data collected over multiple data collection periods to determine a linear regression line (e.g., simple linear regression, least squares regression line, and the like) that best fits the raw STS variation data. The statistical analysis module 103 may also use the raw STS variation data to create one or a collection of histograms. The histogram(s) may be used to determine statistical parameters (e.g., an average, an average deviation, a standard deviation, and the like). A STS trend analysis module 105 utilizes multiple histograms and various statistical parameters to construct a STS trend that can be used to predict future ischemic events in a patient.

The IMD 10 includes an atrial pulse generator 70 and a ventricular/impedance pulse generator 72 to generate pacing stimulation pulses. Microcontroller 60 includes timing control circuitry 79 that is used to control the timing of such stimulation pulses. In order to provide stimulation therapy in a desired number of chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, etc.) by selectively closing the appropriate combination of switches (not shown) as is known in the art. For arrhythmia detection, arrhythmia detector 81 utilizes atrial sensing circuits 82 and ventricular sensing circuits 84 to sense whether a cardiac rhythm is physiologic or pathologic. The atrial sensing circuits 82 and ventricular sensing circuits 84 may also be selectively coupled to the leads through the switch 74 for detecting the presence of cardiac activity in each of the four chambers of the heart. Control signals 86 and 88 from processor 60 direct output of the atrial and ventricular sensing circuits, 82 and 84, that are connected to the microcontroller 60. In this manner, the atrial and ventricular sensing circuits, 82 and 84 are able to trigger or inhibit the atrial and ventricular pulse generators, 70 and 72.

The cardiac signals are applied to the inputs of an analog-to-digital (A/D) data acquisition system 90. The data acquisition system 90 is configured to acquire cardiac signals, convert the raw analog data into a digital cardiac signal, and store the digital cardiac signals in memory 94 for later processing and/or telemetric transmission to an external device 102. Control signal 92 from processor 60 determines when the data acquisition system 90 acquires signals, stores them in memory 94, or transmits data to an external device 102. The data acquisition system 90 is coupled to the right atrial lead 24, the coronary sinus lead 26, and the right ventricular lead 22 through the switch 74 to sample cardiac signals across any combination of desired electrodes.

The microcontroller 60 is coupled to the memory 94 by a suitable data/address bus 96, wherein the programmable operating parameters used by the microcontroller 60 are stored and modified, as required, in order to customize the operation of IMD 10 to suit the needs of a particular patient. The memory 94 may also store data indicative of myocardial function, such as the cardiac data, STS variations, reference STS variations, and STS variation thresholds and the like for a desired period of time (e.g., one hour, 24 hours, or one month). The memory 94 may store instructions to direct the microcontroller 60 to analyze the data to detect ischemia and/or to identify events of interest. For example, the memory 94 (as shown in FIG. 2B) may store STS variation data 120, statistical parameters 121, and STS trends 122. The STS variation data 120 may be the raw STS variations for the patient collected during a data collection period that correspond to a variation in the STS that exceeds a predetermined threshold. The statistical parameters 121 are created by the statistical analysis module 103 (shown in FIG. 1) may be derived from a histogram 400 (shown in FIG. 4), and the statistical parameters may include an average, an average deviation, a standard deviation, and the like. The statistical parameters 121 may also correspond to multiple histograms (as shown in FIG. 5), which have the STS variations sorted according to heart rate bins (e.g., less than 40 beats per minute (bpm), 40-60 bpm, 60-90 bpm, and greater than 90 bpm) for a particular data collection period. The STS trends 122 are created by the STS trend analysis module 105 (shown in FIG. 2A) and are described below.

The operating parameters of the IMD 10 may be non-invasively programmed into the memory 94 through a telemetry circuit 100 in communication with the external device 102, such as a programmer (shown in FIG. 12), trans-telephonic transceiver or a diagnostic system analyzer. The telemetry circuit 100 is activated by the microcontroller 60 by a control signal 106. The telemetry circuit 100 allows cardiac signals, and status information relating to the operation of IMD 10 (as contained in the microcontroller 60 or memory 94) to be sent to the external device 102 through an established communication link 104.

The IMD 10 additionally includes a battery 110, which provides operating power to all of the circuits shown within the housing 46, including the processor 60. The IMD 10 is shown as having an impedance measuring circuit 112 which is enabled by the microcontroller 60 via a control signal 114. The impedance measuring circuit 112 is advantageously coupled to the switch 74 so that impedance at any desired electrode may be obtained. The IMD 10 also includes a physiologic sensor 108 that may be used to adjust pacing stimulation rate according to the exercise state of the patient.

In the case where IMD 10 is intended to operate as an implantable cardioverter/defibrillator (ISCD) device, the IMD 10 detects the occurrence of an STS variation that indicates an arrhythmia, and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules) or high energy (11 to 40 joules), as controlled by the microcontroller 60. Such shocking pulses are applied to the heart 11 of the patient through at least two shocking electrodes, and as shown in this embodiment, selected from the left atrial coil electrode 36, the RV coil electrode 42, and/or the SVC coil electrode 44.

Figure 3:
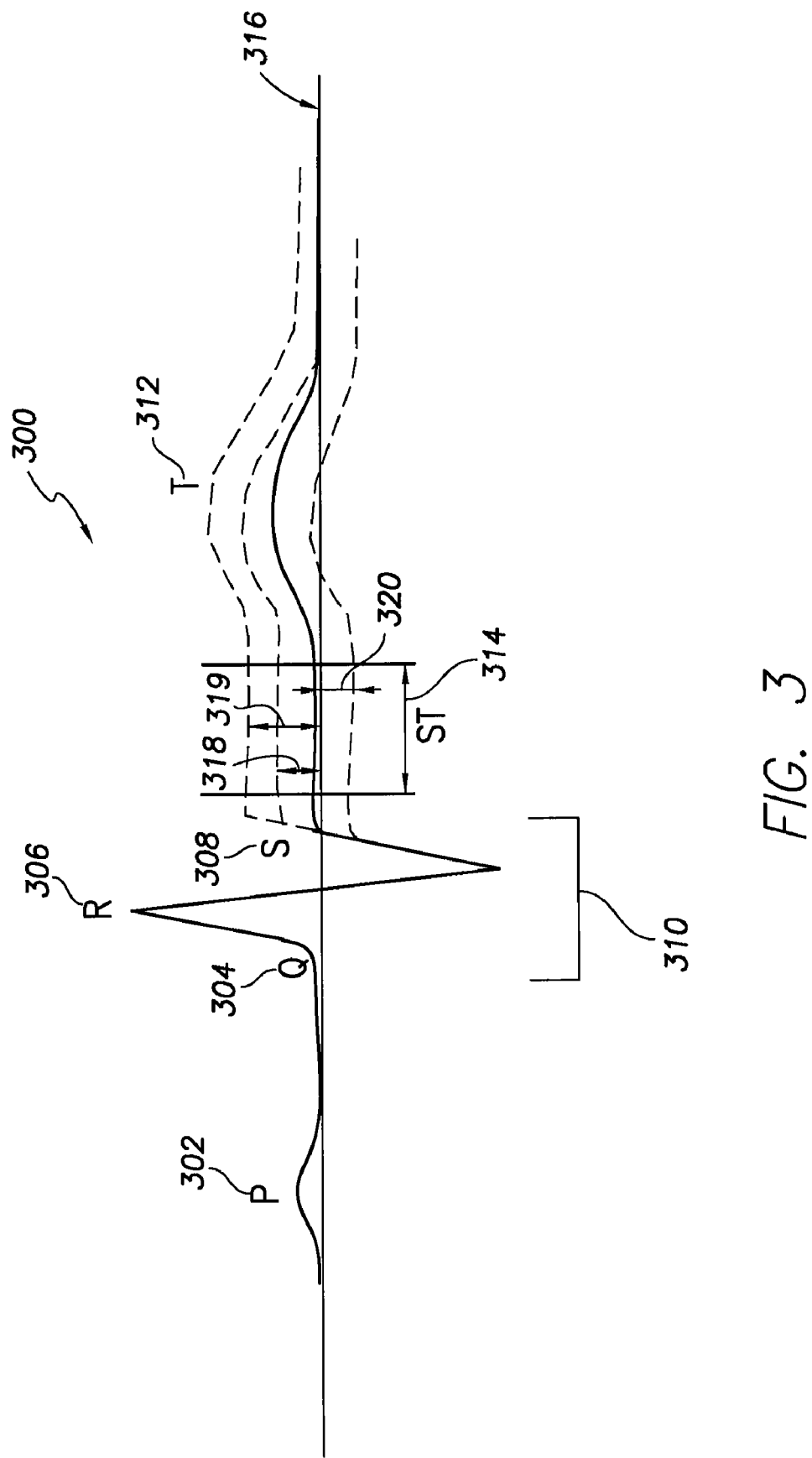
FIG. 3 illustrates an exemplary diagram of a typical electrocardiogram and potential STS variations utilized in accordance with an embodiment of the present invention.

FIG. 3 illustrates a single cardiac cycle 300 composed of a P-wave 302, a Q-wave 304, an R-wave 306, an S-wave 308 and a T-wave 312. The cardiac cycle 300 may represent cardiac signals, such as intra-cardiac electrogram (IEGM) signals, electrocardiogram (ECG) signals and the like. The horizontal axis represents time, while the vertical axis is defined in units of voltage. An abnormal cardiac signal indicates a potential ischemic condition. The cardiac cycle is composed of a Q-wave 304, an R-wave 36 and an S-wave 308, which together make a QRS complex 310. The QRS complex 310 is used to locate the R-wave 306 to determine a baseline 316. The portion of the signal between the S-wave 308 and T-wave 312 constitutes a ST segment 314. As shown, the ST segment 314 may have a voltage level that aligns with the voltage level of the baseline 316. Alternatively, the ST segment 314 may have a voltage level that is shifted above 318, 319 or shifted below 320 the baseline 316. ST segment variations may occur above or below the baseline 316. Alternatively, ST segment variations may include ST deviations or ST shifts. A ST deviation is determined by subtracting the level of a PQ segment 303 from the level of the ST segment 314 for one heartbeat. The ST deviation provides a measure of the change in variability over a period of time. An ST shift is determined by changes in the ST deviation over a period of time. For example, a current ST shift may be calculated by subtracting a stored baseline ST deviation from a newly acquired ST deviation. ST deviations and ST shifts may be calculated as averages over multiple cardiac cycles as well. Deviations of the voltage level of the ST segment 314 may be a result of injury to cardiac muscle, changes in the synchronization of ventricular muscle depolarization, drug or electrolyte influences, and the like. The voltage elevation of the ST segment, as shown by 318 and 319, in a cardiac signal may result when there are abnormalities in the polarizations of cardiac tissue during an acute myocardial infraction (MI). The STS variations 318-320 may arise because of differences in the electrical potential between cells that have become ischemic and those that are still receiving normal blood flow. Thus, the STS variations 318-320 are a reliable indicator of the possibility of ischemia. It is recognized that ST segment 314 may deviate due to non-ischemic events.

Figure 4:
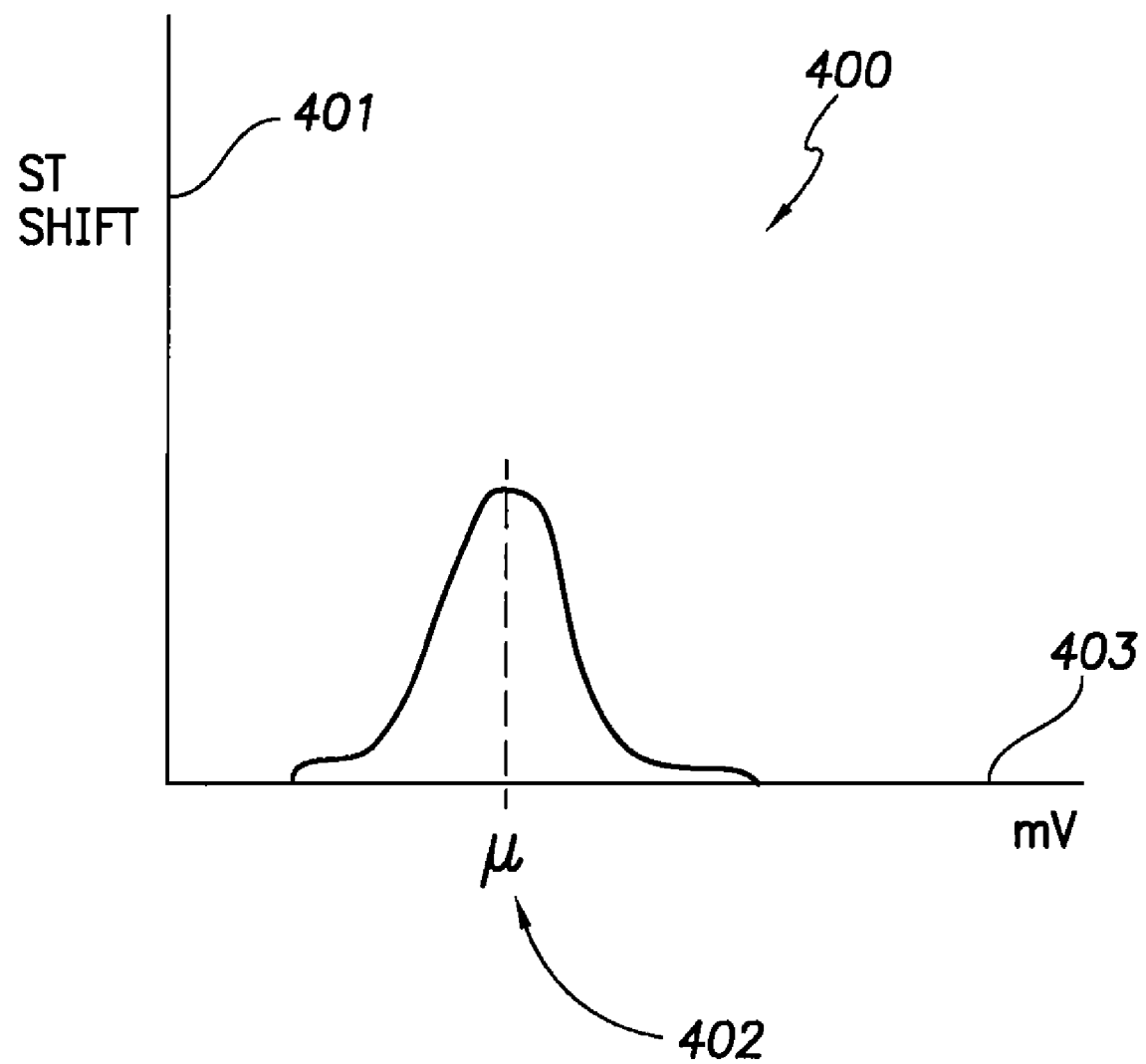
FIG. 4 illustrates a histogram of ST segment variations utilized in accordance with an embodiment of the present invention.
Figure 5:
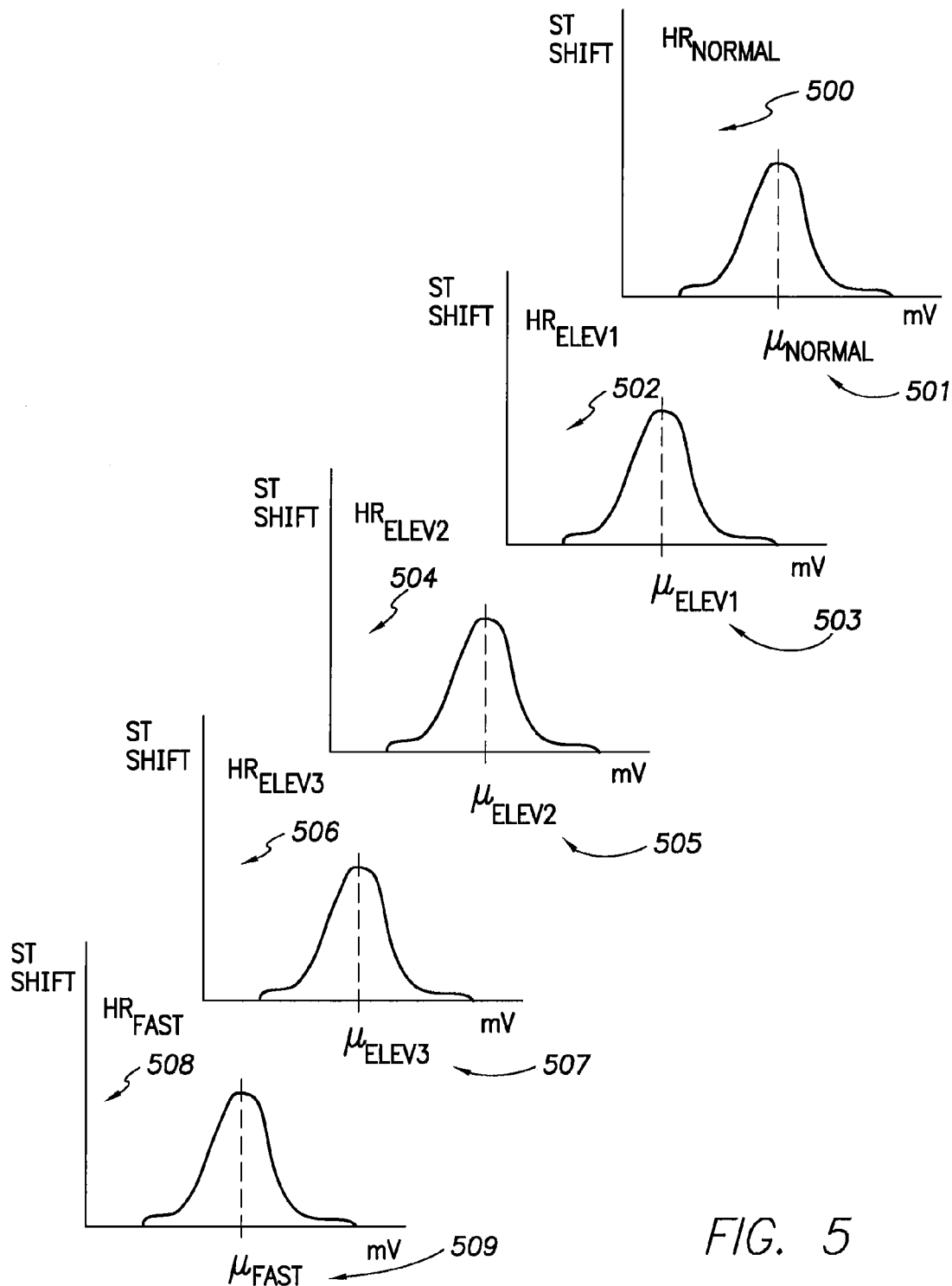
FIG. 5 illustrates a set of histograms for multiple data collection periods from which statistical parameters are derived in accordance with an embodiment of the present invention.

FIG. 4 illustrates a histogram 400 that may be used in connection with statistically determining the variability of an STS variation. The histogram 400 is constructed and utilized to analyze the variability of STS variations 318-320 (FIG. 3) for a particular patient (or a group of patients) caused by non-ischemia related events and ischemia related events. First, STS variations 318-320 are collected over a data collection period (e.g. a day, seven days, a month) for the patient, and stored in memory 94 as STS variation data 120. The histogram 400 plots, on the vertical axis 401, the number of times a STS variation 318-320 occurs, and plots on the horizontal axis 403 the voltage value associated with a particular STS variation 318-320. Once the histogram 400 is constructed, certain statistical parameters can be analyzed, such as the average 402 or alternatively the average deviation (not shown), standard deviation (not shown) and the like.

FIG. 5 illustrates a set of histograms 500. 502. 504, 506, and 508 for a particular data collection period where the data has been separated into various heart rate bins or ranges (e.g., <35 bpm, 35-75 bpm, 75-105 bpm, 105-125 bpm, and >125 bpm) from which statistical parameters may be derived. Each histogram 500, 502, 504, 506 and 508 represent a series of STS variations 318-320 that occur for a particular heart rate bin or range during a particular data collection period (e.g., seven days). At least one data collection period may fully or partially occur before the implant of ICD 10 to create a baseline for the patient. The baseline allows a physician to monitor a patient's progress and to determine how well the implant is functioning. The data collection periods can be repeated in a cyclic manner (e.g., 1-7 days after implant, 23-30 days after implant, 53-60 days after implant, 83-90 implant, and the like). Other data collection periods (e.g., one day, three days, five days, ten days, fourteen days, and the like) may be selected. The data collection period may be determined by a user, but the data collection period must be less than 30 days in order not to mask the STS variations.

The data collection periods are separated by an interval of time (e.g., one month, four months, six months, and the like) before another successive data collection period begins. For each data collection period, multiple histograms are created. A histogram is created for a particular range of heart rates. For example, histogram 500 represents STS variations that occur in a patient during a normal heart rate (e.g., 35-60 beats per minute). Histogram 502 represents STS variations that occur in a patient during an elevated heart rate (e.g., 61-80 beats per minute). Histogram 504 represents STS variations that occur in a patient during another elevated heart rate (e.g., 81-100 beats per minute). Histogram 506 represents STS variations that occur in a patient during still another elevated heart rate (e.g., 101-130 beats per minute). Histogram 508 represents STS variations that occur in a patient having a fast heart rate (e.g., greater than 130 beats per minute).

Each histogram 500, 502, 504, 506 and 508 includes a statistical parameter. The statistical parameter may be, for example, an average, an average deviation, or a standard deviation. The user selects which statistical parameter is to be used. For the histograms 500, 502, 504, 506, and 508 a mean value is shown for each histogram: $\mu_{NORM}$ 501, $\mu_{ELEV1}$ 503, $\mu_{ELEV2}$ 505, $\mu_{ELEV3}$ 507, $\mu_{FAST}$ 509. The mean values 501, 503, 505, 507, and 509 are stored in memory 94 as statistical parameters 121 (see FIG. 2B), and the mean values 501, 503, 505, 507 and 509 corresponding to each respective histogram 500, 502, 504, 506, an 508 form a statistical parameter set for a particular data collection period. The statistical parameter set is utilized by the STS Trends module 122 (shown in FIG. 2A) to construct a STS trend.

Figure 6:
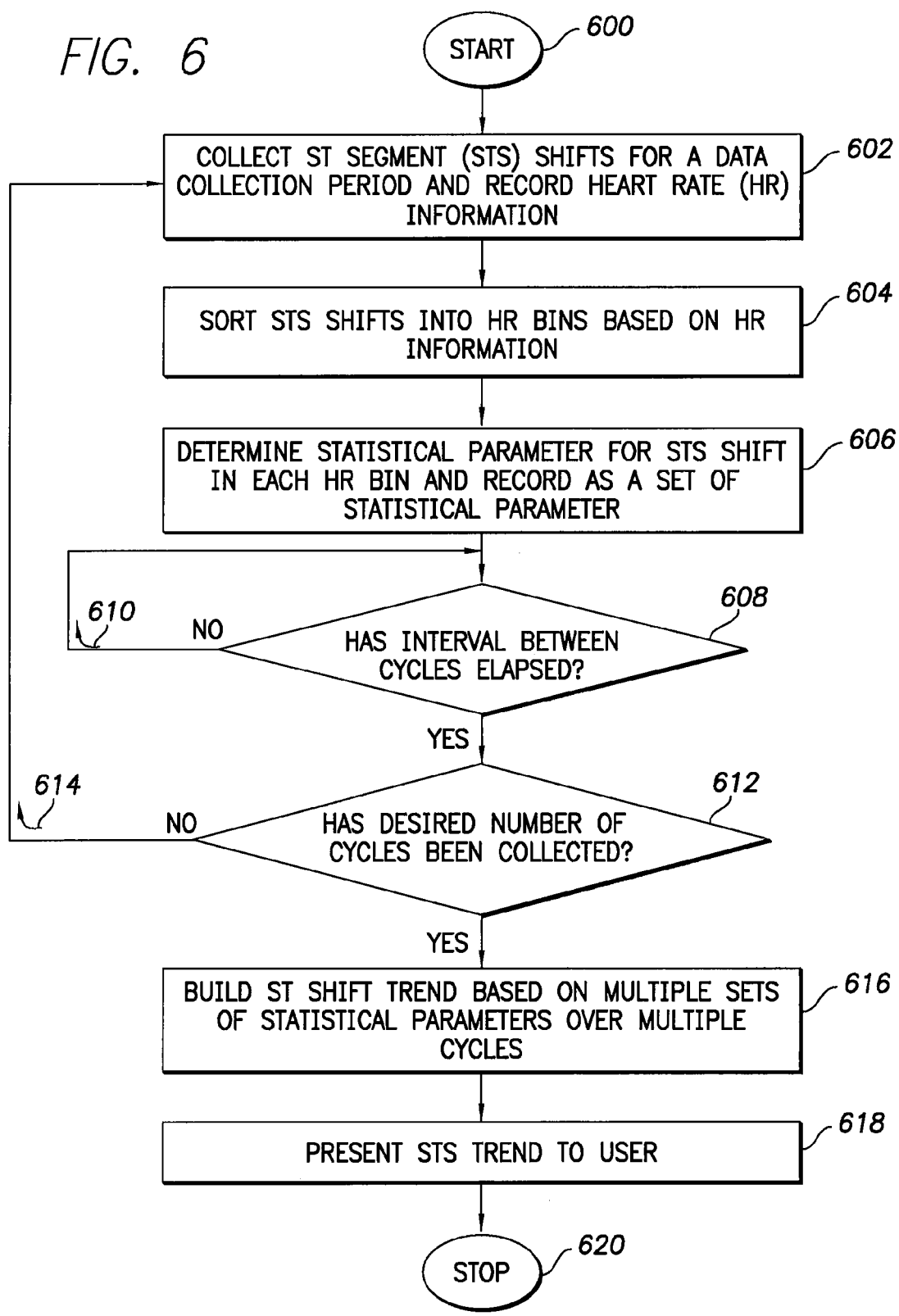
FIG. 6 illustrates a flow diagram for determining STS Trends in accordance with an embodiment of the present invention.

FIG. 6 illustrates a flow diagram 600 that depicts a process for determining a STS trend 630 (shown in FIG. 7) in accordance with an embodiment of the present invention. At 602, the process collects STS variations 318-320 (shown in FIG. 3) for a data collection period. The data collection period for the STS trend 630 is seven days. But the data collection period may be any user selected period (e.g., one day, a three day period, a seven day period, a ten day period a fourteen day period, or any combination of days that is less than a 30 day period). Data collected for more than 30 consecutive days may mask STS variations. Each STS variation value includes a corresponding heart rate value. Both the STS variation and the heart rate values are stored as STS data 120 in memory 94 (shown in FIG. 2B).

At 604, the STS data 120 is sorted into multiple heart rate bins. As mentioned above, each STS variation value collected during a data collection period has a corresponding heart rate value. A user selects the heart rate bins into which the STS data 120 is to be sorted. The heart rate bins are based on a range of heart rates (e.g., a low heart rate, a normal resting heart rate, a normal active heart rate, an elevated heart rate, a fast heart rate, an arrhythmic heart rate, and a bradycardia heart rate, and the like). The range of heart rates for each bin is also user selectable. For instance, the user may select the normal heart rate bin (e.g., NORM) to range from 35 to 60 beats per minute, or the user may select the normal heart bin to range from 50 to 80 beats per minute. Furthermore, multiple elevated heart rate conditions may be chosen. For example, one elevated heart rate bin (e.g., ELEV1) may include heart rates ranging from 60 to 80 beats per minute while another elevated heart rate bin (e.g., ELEV2) may include heart rates ranging from 81 to 100 heart rates per minute and still another bin (e.g., ELEV3) may include heart rates ranging from 101 to 130 beats per minute. A fast heart rate bin (e.g., FAST) may be selected to have heart rates in the range of greater than 130 beats per minute. The STS variations are then sorted according to their respective heart rates. For instance, an STS variation of −1.0 mV measured at 86 bpm is placed into the Normal resting heart rate bin, while an STS variation of −25 mV measured at 121 bpm is placed into the ELEV3 bin. Once the STS variation values have been sorted by heart rate, a histogram (as shown in FIG. 5) for each heart rate bin may be created.

At 606, the statistical analysis module 103 within the programmable micro-controller 60 (shown in FIG. 2A) determines statistical parameters 121 for the STS variations that are sorted into heart rate bins. The statistical parameter may include: an average, an average deviation, a standard deviation, and the like. The user may select which statistical parameter is to be determined. The statistical analysis module 103 mathematically determines a statistical parameter, such as the mean, based on the STS variation values stored in STS data 120, for each heart rate bin. For each data collection period, the set of statistical parameters for each heart rate bin are stored as statistical parameters 121 in memory 94 (shown in FIG. 2B).

At 608, the programmable micro-controller 60 (shown in FIG. 2A) checks to see if the interval between cycles has elapsed. In order to create a STS trend 630 (shown in FIG. 7), multiple data collection periods are gathered. A cycle corresponds to the data collection period separated by an interval until the next data collection period. Thus, each data collection period is separated by a user defined interval of time. A cycle measures the time from the beginning of the data collection period until the lapse of the interval of time before a new data collection period begins. The data collection period may begin before the implant of ICD 10, and therefore, the cycle may begin before surgery. The interval may also begin one day after the implant of ICD 10 or a week after implant of ICD 10. Alternatively, the interval may be a thirty day period, a sixty day period, a ninety day period, a one-hundred-twenty day period. If the interval between cycles has not elapsed, flow continues along 610 and repeats at 608. If the interval has elapsed, the process continues to 612.

At 612, the programmable micro-controller 60 (shown in FIG. 2A) checks to see if the desired number of cycles has been collected. A user may select to collect two or more cycles in order to create a STS trend 630. The closeness of the cycles to one another will affect the accuracy of the STS trend 630. If a user does not allow enough time to elapse between data collection periods, the ST segments will mask a possible abnormal physiology. Thus, cycles should be selected to be at least thirty days apart. If the desired number of cycles has not been collected, then flow continues along 614 back to 602. If the desired number of cycles has been collected, then the process continues to 616.

At 616, the STS trend analysis module 105 within the programmable micro-controller 60 (shown in FIG. 2A) constructs STS trends 122 for each cycle based on multiple sets of statistical parameters 121. STS trends 122 are stored in memory 94 (shown in FIG. 2B). The STS trend analysis module 105 then uses the STS trends 122 for each cycle to build a STS trend 630 (shown in FIG. 7).

At 618, the STS trend 630 is presented to the user. The STS trend 630 may be presented as a display, a pictorial representation, a symbolic representation, a graph, a bar graph, a chart, a histogram, a pie chart, a Venn diagram, and combinations thereof. The STS trend 630 may indicate an abnormal physiology, such as an ischemia, a myocardial infarction, a post-myocardial infarction, a silent myocardial infarct, an arrhythmia, a fibrillation, a heart block or a congestive heart failure. At 620, the process terminates or can be repeated by the user.

Figure 7:
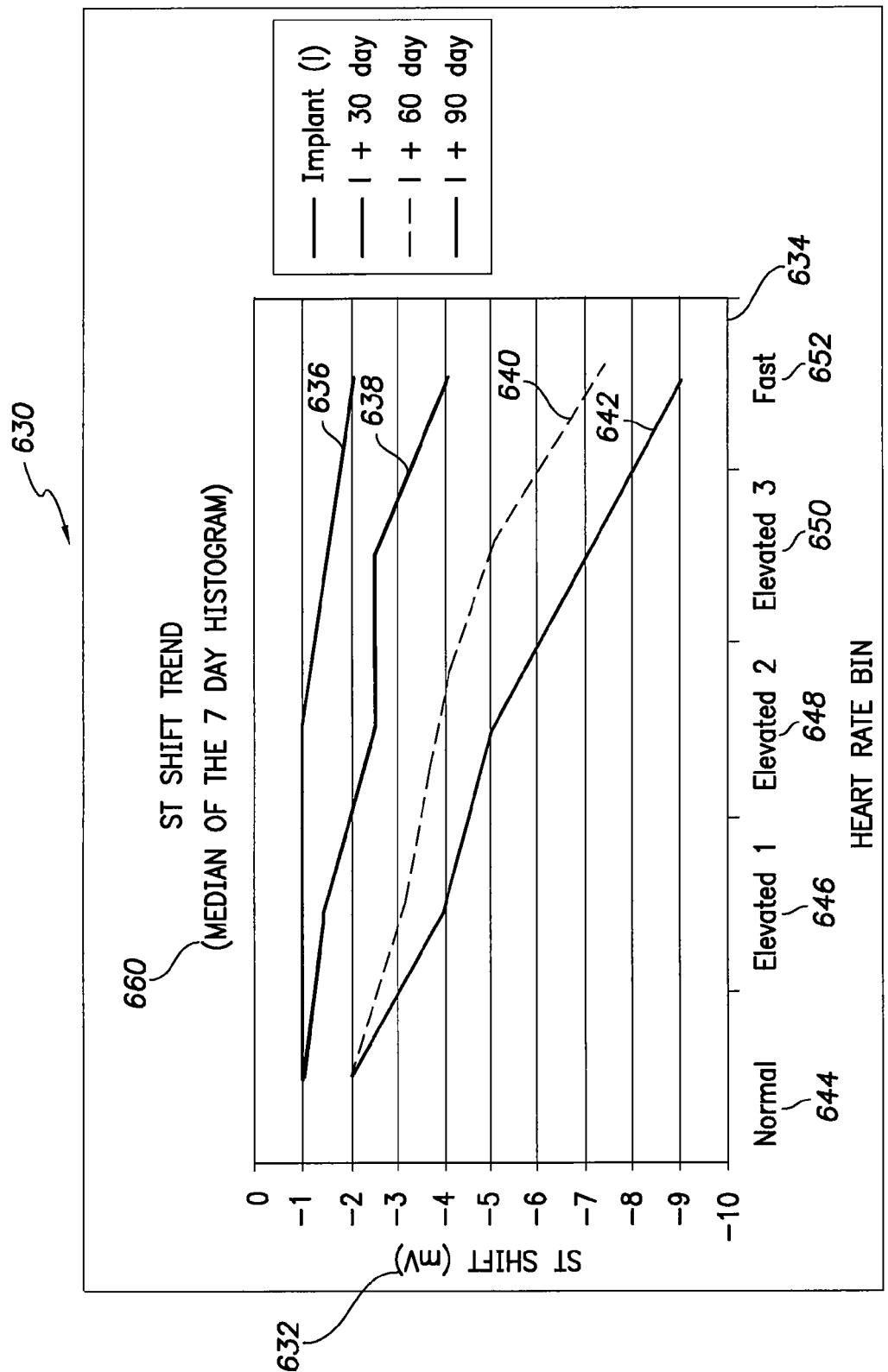
FIG. 7 illustrates a STS Trend in accordance with an embodiment of the present invention.

FIG. 7 illustrates a ST variation trend 630 for a particular patient in accordance with an embodiment of the present invention. The STS trend 630 is a graph of the statistical parameter 121 of multiple STS variations that were collected during a data collection period (e.g., seven days) plotted against a heart rate bin for the STS variations. The horizontal axis 634 represents the heart rate bin associated with a particular STS variation, and the vertical axis 632 represents the ST variation value in milli-volts. As shown on the horizontal axis 634, the heart rate bins are a normal bin 644, an elevated1 bin 646, an elevated2 bin 648, an elevated3 bin 650 and a fast bin 652. The normal bin 644 corresponds to a heart rate ranging between 35 and 60 beats per minute. The elevated1 bin 646 corresponds to a heart rate ranging between 61-80 beats per minute. The elevated2 bin 648 corresponds to a heart rate ranging between 81-100 beats per minute. The elevated3 bin 650 corresponds to a heart rate ranging between 101-130 beats per minute. The fast1 bin 652 corresponds to a heart rate faster than 130 beats per minute. The STS trend 630 shows multiple cycles separated by a thirty (30) day interval. Cycle 636 represents STS variations that occurred after implant. Cycle 638 represents STS variations that occurred 30 days after implant. Cycle 640 represents STS variations that occurred 60 days after implant, and cycle 642 represents STS variations that occurred 90 days after implant.

The statistical parameter depicted in STS trend 630 is the median value 660 of the STS variations. The STS trend 630 shows that the median values of the STS variation decreased from the time the implantable medical device was implanted in the patient. At a normal heart rate the STS variation decreased from −1 mV to −2 mV (e.g., normal bin 644). However as the heart rate increased the median ST variation decreased further. Elevated1 bin 646 (e.g., 60-80 bpm) indicates that the median STS variation decreased from −1 mV to −4 mV over a 90 day period. Elevated2 bin 648 (e.g., 81-100 bpm) indicates that the median STS variation decreased from −1 mV to −5 mV over a 90 day period. Elevated3 bin 650 (e.g., 101-130 bpm) indicates that the median STS variation decreased from −1.5 mV to −7 mV over a 90 day period, and fast bin 652 (e.g., greater than 130 bpm) indicates that the median STS variation decreased from −2 mV to −9 mV over a 90 day period.

Figure 8:
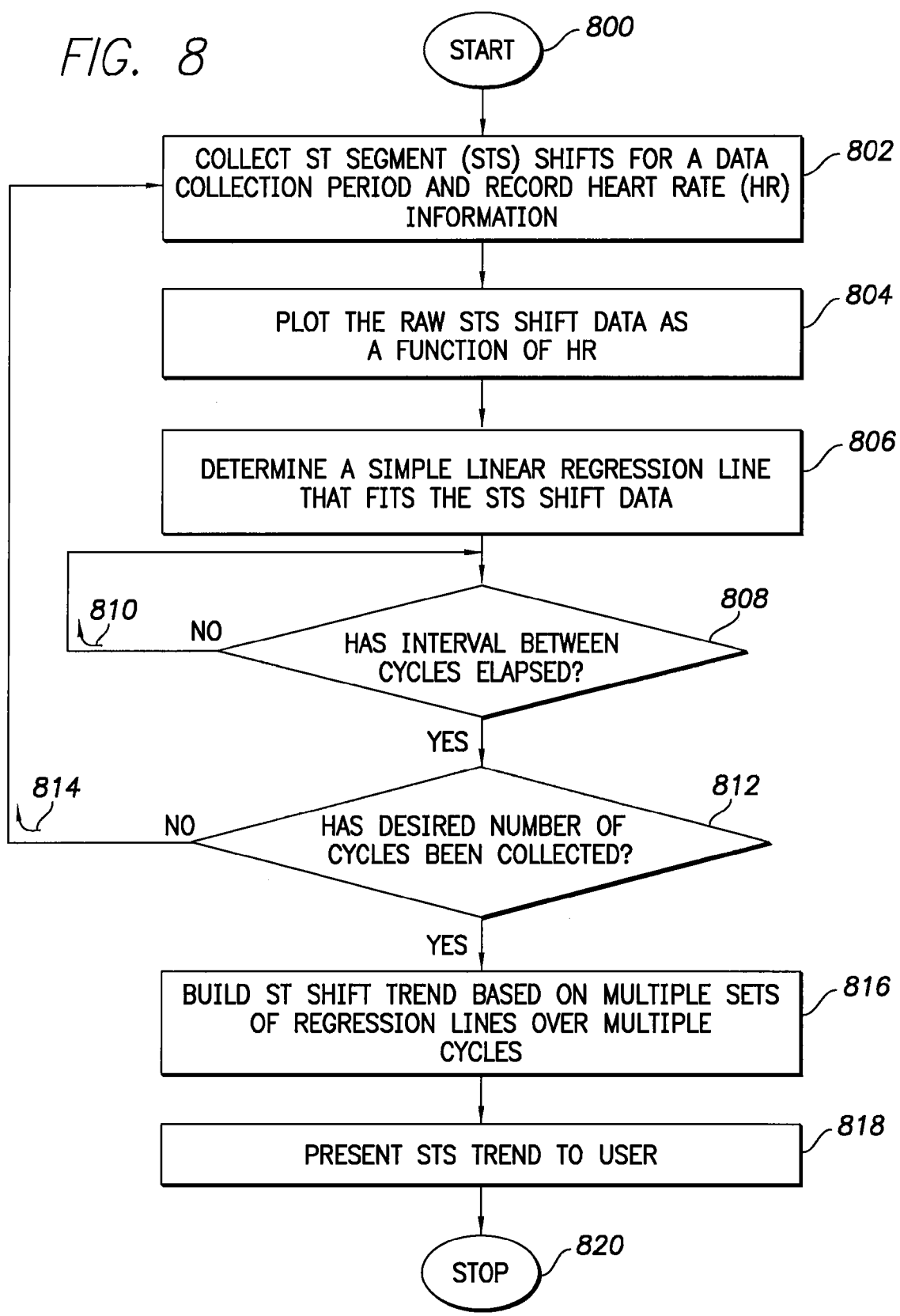
FIG. 8 illustrates a flow diagram for determining STS Trends based on a linear regression through a data set in accordance with an embodiment of the present invention.

FIG. 8 illustrates a flow diagram 800 for determining ST variation trends 900 (shown in FIGS. 9, 10, and 11) based on a linear regression through a data set of STS variations in accordance with an embodiment of the present invention. At 802, the process collects STS variations for a data collection period. The data collection period comprises at least one day, a three day period, a seven day period, a ten day period a fourteen day period, or any combination of days. Each STS variation value includes a corresponding heart rate value. Both the STS variation and the heart rate are stored as STS data 120 in memory 94 (shown in FIG. 2B).

At 804, the STS data 120 is plotted as a function of heart rate. During a data collection period multiple samples of raw STS variations are collected and stored in memory 94 as STS data 120. Each STS variation value has a corresponding heart rate. Typically, the heart rate range is from 30 to 135 beats per minute (bpm) and the STS variation values range from +5 to −25 mV. The programmable micro-controller 60 graphs the STS variation data 120 against the heart rate for a particular data collection period (See FIGS. 9, 10, and 111).

At 806, the programmable micro-controller 81 (shown in FIG. 2A) has the statistical analysis module 103 determine statistical parameters (e.g., perform a regression analysis) of the STS data 120. Alternatively, the statistical analysis module 103 may perform a simple linear regression, a least squares linear regression, a robust regression, a multiple linear regression, a nonlinear regression, or a maximum likelihood estimation. The values of the regression analysis are stored as statistical parameters 121 in memory 94 (shown in FIG. 2B). Once the statistical parameters (e.g., values of the regression analysis) are determined for a particular data collection period, a linear regression line is determined that best fits the STS variation data 120 (See FIGS. 9, 10, and 11). The values of the linear regression line are stored as STS trends 122 in memory 94.

At 808, the programmable micro-controller 60 (shown in FIG. 2A) checks to see if the interval between cycles has elapsed. In order to create a STS trend (shown in FIGS. 9, 10, and 11) using regression analysis, multiple cycles are collected. The cycles may begin before surgery to monitor a patient's progression or the cycles may begin after an ICD 10 device is implanted. Each data collection period is separated by an interval of time before the next cycle begins. The interval of time between data collection periods may be selected by the user. For instance the interval may be one of a day after implant of ICD 10 or a week after implant of ICD 10. Alternatively, the interval may be a thirty day period, a sixty day period, a ninety day period, a one-hundred-twenty day period. If the interval between cycles has not elapsed, flow continues along 810 and repeats at 808. If the interval has elapsed, the process continues to 812.

At 812, the programmable micro-controller 60 (shown in FIG. 2A) checks to see if the desired number of cycles has been collected. A cycle corresponds to the data collection period separated by an interval until the next data collection period. A user may select to collect two or more cycles in order to create a STS trend 900 (shown in FIGS. 9, 10, and 11) using regression analysis. If the desired number of cycles has not been collected, then flow continues along 814 back to 802. If the desired number of cycles has been collected, then the process continues to 816.

At 816, the programmable micro-controller 60 (shown in FIG. 2A) has the STS trend analysis module 105 graph the multiple STS trends 122 stored in memory 94 to build an STS trend. The STS trends 122 corresponding to a particular cycle are retrieved from memory 94. For each cycle, the STS trends 122 include the values of the regression analysis (performed in step 806). The STS trend analysis module 105 then graphs the values of the linear regression line for that cycle over the graph of the raw ST variations for the corresponding cycle. When all the cycles have been graphed, a STS trend 900 is depicted (shown in FIGS. 9, 10, and 11).

At 818, the STS trend 900 (shown in FIGS. 9, 10 and 11) is presented to the user as a graph or a chart. The STS trend 900 may indicate an abnormal physiology, such as an ischemia, a myocardial infarction, a post-myocardial infarction, a silent myocardial infarct, an arrhythmia, a fibrillation, a heart block or a congestive heart failure. At 820, the process terminates or can be repeated by the user.

Figure 9:
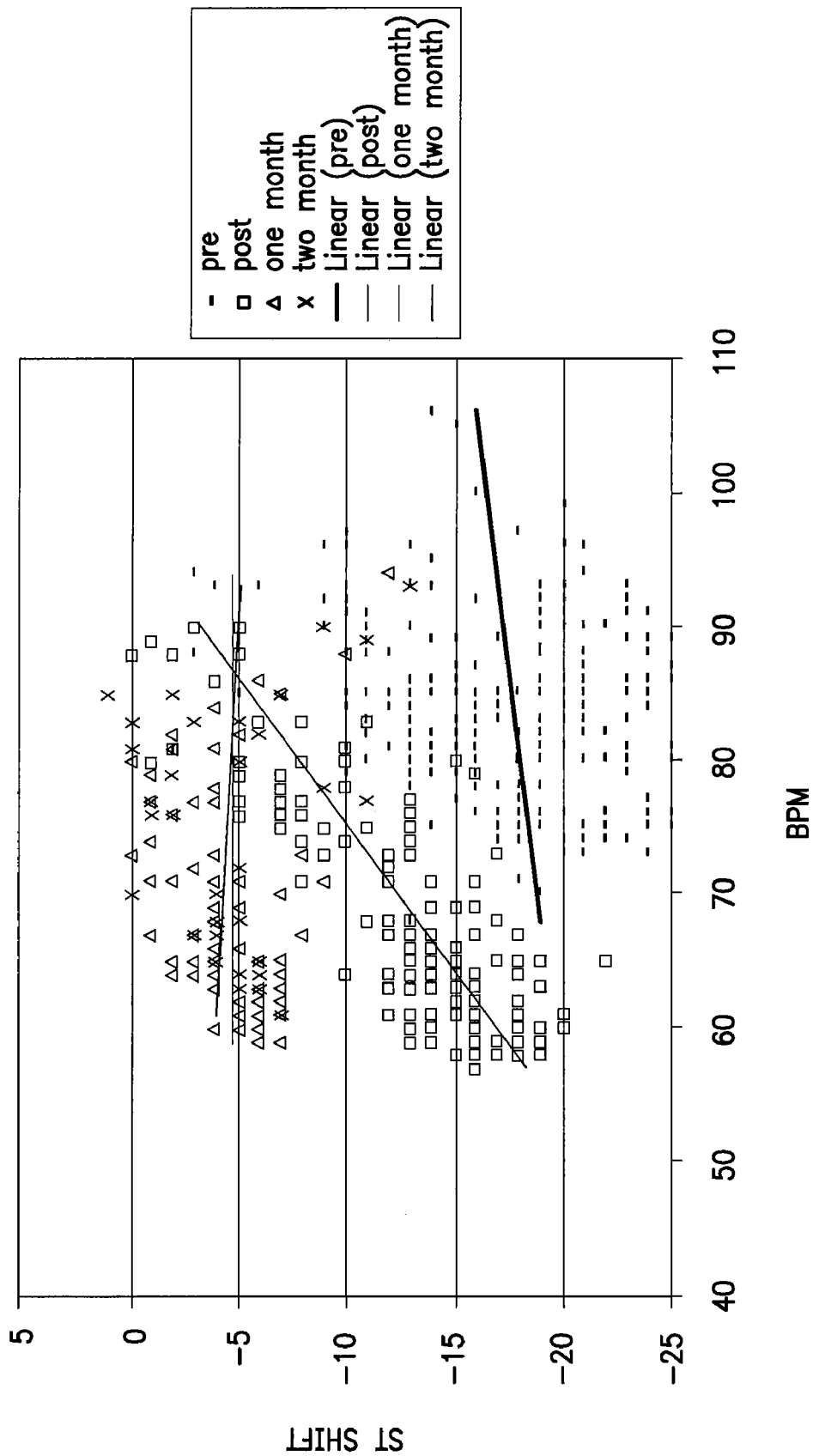
FIGS. 9, 10, and 11 illustrate exemplary STS Trends of different patients utilizing linear regression in accordance with an embodiment of the present invention.
Figure 10:
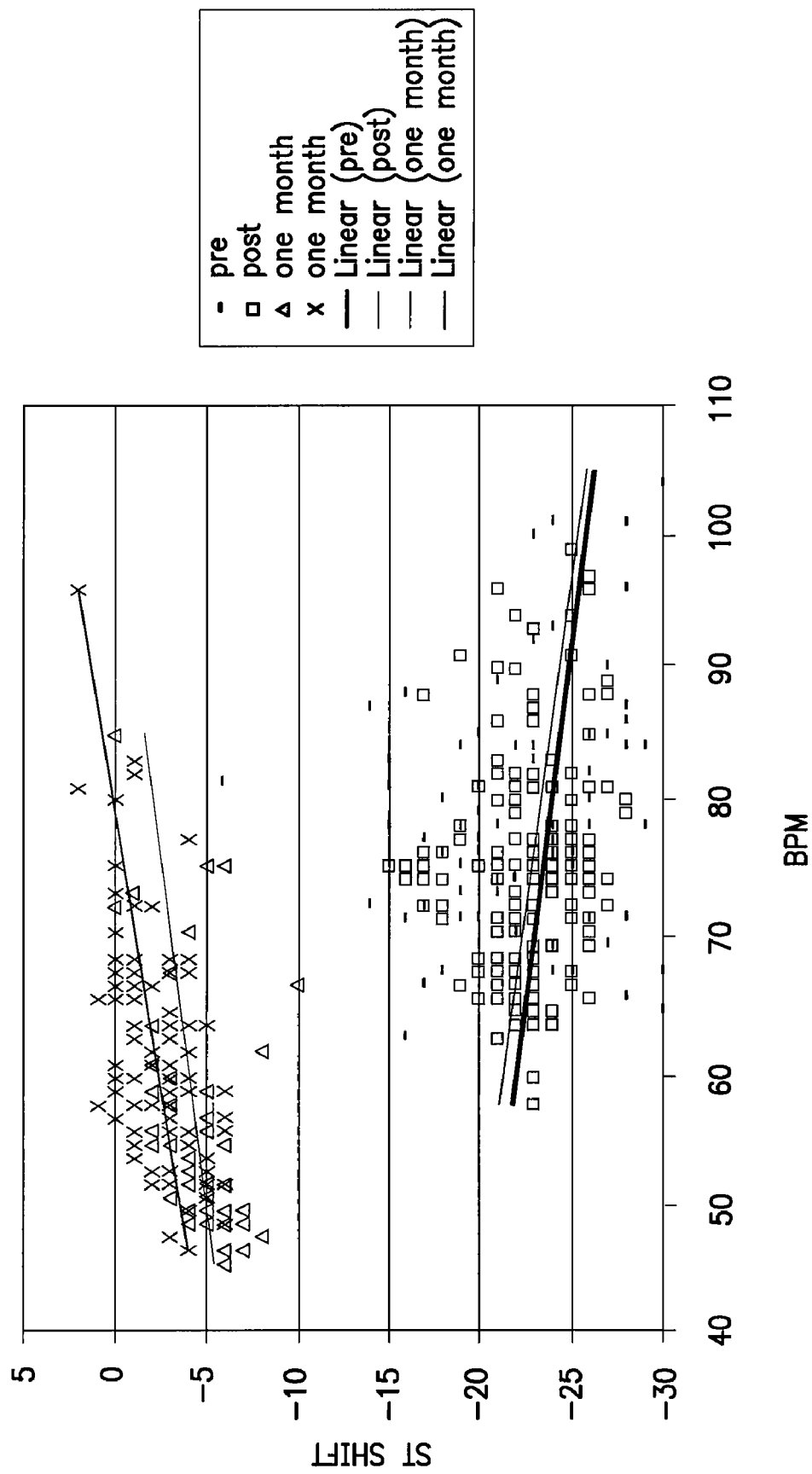
Figure 11:
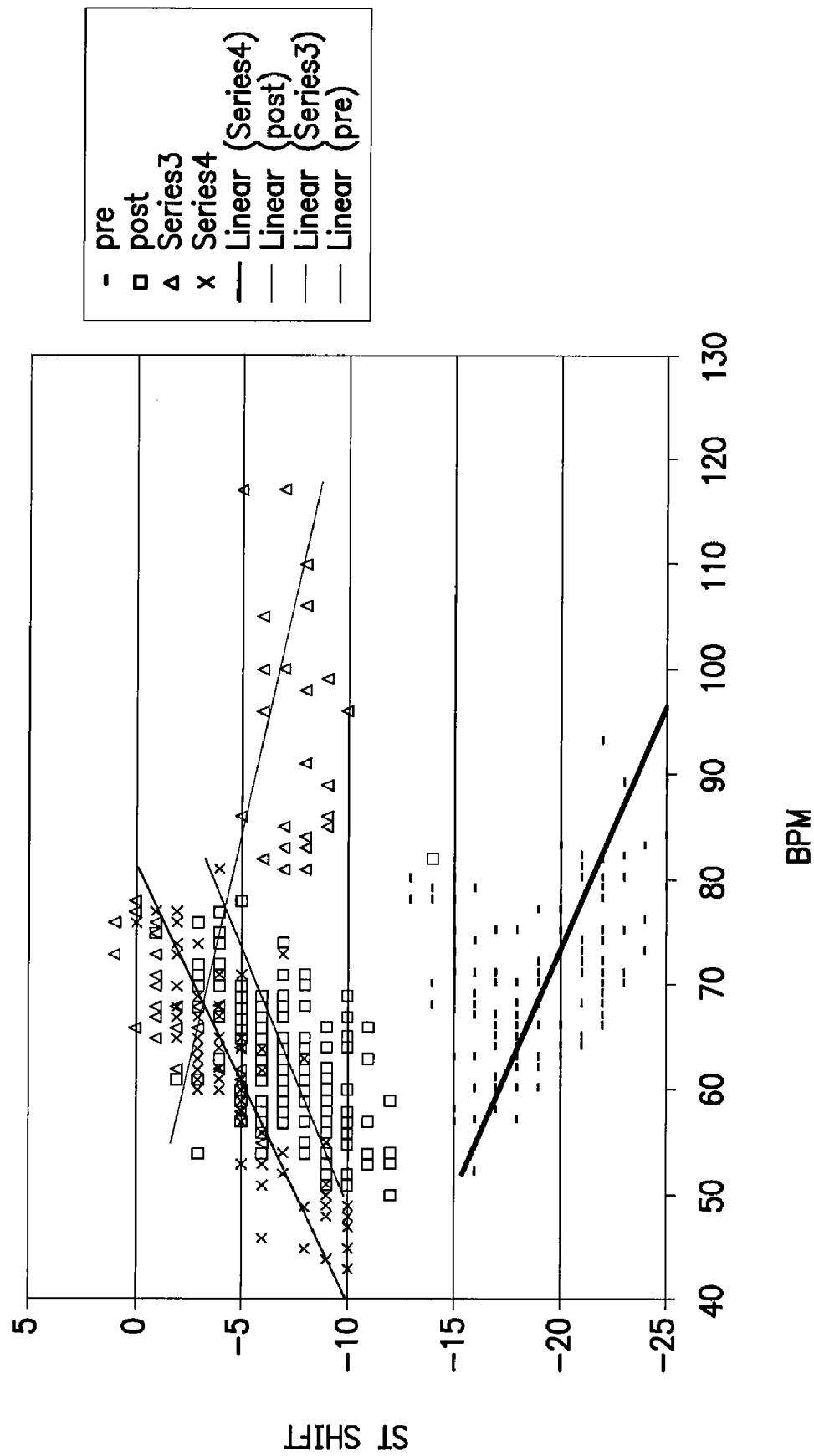

FIGS. 9, 10, and 11 illustrate exemplary STS trends 900, 902 and 904 of different patients utilizing linear regression in accordance with an embodiment of the present invention. FIGS. 9, 10, and 11 are charts of the raw STS variation value and the corresponding heart rate for multiple cycles. The horizontal axis 906 represents a heart rate (defined in beats per minute (bpm)), while the vertical axis 908 represents a STS variation value (defined in units of voltage). The STS variations are plotted based on the time period when the STS variations were acquired (e.g., pre-implant, post-implant, one month after implant, two months after implant). STS variations acquired prior to the implant of ICD 10 (e.g., pre-implant 910) are shown as a solid black square. STS variations acquired after the implant of ICD 10 (e.g., post-implant 912) are shown as a hollow square. STS variations acquired one month after implant (e.g., one month 914) are shown as a hollow triangle. STS variations acquired two months after implant (e.g., two month 916) are shown as a cross.

FIG. 9 shows STS trend 900 that depicts a patient whose STS variations increased after the implant of an implantable medical device (e.g., implantable cardiac defibrillator). The pre-implant regression line 920 shows that the STS variation increased from −19 mV to −14 mV with a corresponding increase in heart rate between 70 bpm to 108 bpm, respectively before surgery. After the implant of the ICD 10 (e.g., implantable cardiac defibrillator), the STS variation increased significantly in an upward direction (e.g., increasing STS variation values with increasing heart rate) as shown by post-implant regression line 922 having STS variations ranging from −18 mV to −3 mV with a corresponding heart rate between 57 bpm to 90 bpm. One month after the implant, the STS variation started to stabilize. As shown by a one month regression line 924, the STS variations are about the −4 mV value with the heart rate from 58 to 91 bpm. Two months after the implant the STS variations remained stable as shown by a two month regression line 926. The STS variation values are about −5 mV with the heart rate from 58 to 91 bpm.

FIG. 10 shows STS trend 902 that depicts a patient whose STS variations increased after the implant of ICD 10 (e.g., implantable cardiac defibrillator). The pre-implant regression line 930 shows that the STS variation dropped from −22 mV to −26 mV with a corresponding heart rate between 57 bpm to 105 bpm before surgery. After the implant of the ICD 10, the STS variation increased slightly, as shown by post-implant regression line 932, but the STS variation dropped from −21 mV to about −26 mV with a corresponding heart rate between 57 bpm to 105 bpm. Both the pre-implant regression line 930 and the post-implant regression line 932 are parallel to one another and are heading in a down-ward direction (e.g., decreasing STS variations with increasing heart rate). However, one month after the implant, the STS variation increased in a positive direction. As shown by a one month regression line 934, the STS variation values increased from −4 mV to 3 mV with a heart rate between 45 bpm to 88 bpm. Two months after the implant the STS variations remained positive. A two month regression line 936 shows the STS variation values ranging from the −4 mV to +3 mV with a heart rate from 46 to 96 bpm. Both the one month regression line 934 and the two month regression line 936 are parallel to one another in an upward positive direction (e.g., increasing STS variations with increasing heart rate).

FIG. 11 shows STS trend 904 that depicts a patient whose STS variations increased after the implant of ICD 10 (e.g., implantable cardiac defibrillator). The pre-implant regression line 940 shows that the STS variation dropped from about −15.5 mV to −25 mV with a corresponding heart rate of between 50 bpm to 98 bpm, respectively before surgery. The STS variations decreased in a downward direction as the heart rate increased. After the implant of the implantable medical device, and as shown by post-implant regression line 942, the STS variation increased in an upward direction. The STS variations range from about −10 mV to −4 mV with corresponding heart beats between 50 bpm to 82 bpm. The pre-implant regression line 940 and the post-implant regression line 942 diverged from one another, with the pre-implant regression line 940 heading in a downward direction with decreasing values of STS variations with increased heart rate, and the post-implant regression line 942 heading in an opposite upward direction with increasing values of STS variations with increased heart rate. One month after implant, the STS variation decreased with increasing heart rate. The one month regression line 944 is similar to the pre-implant regression line 942 in direction (e.g., decreasing STS variations with increased heart rate). The one month regression line 944 showed a downward progression of STS variations with the STS variation values ranging from −2 mV to −9 mV with a heart rate between 56 bpm to 119 bpm. Two months after the implant the STS variations changed again. The two month regression line 946 showed an upward increase in STS variation from −10 mV to OmV with the heart rate between 40 bpm to 81 bpm.

Figure 12:
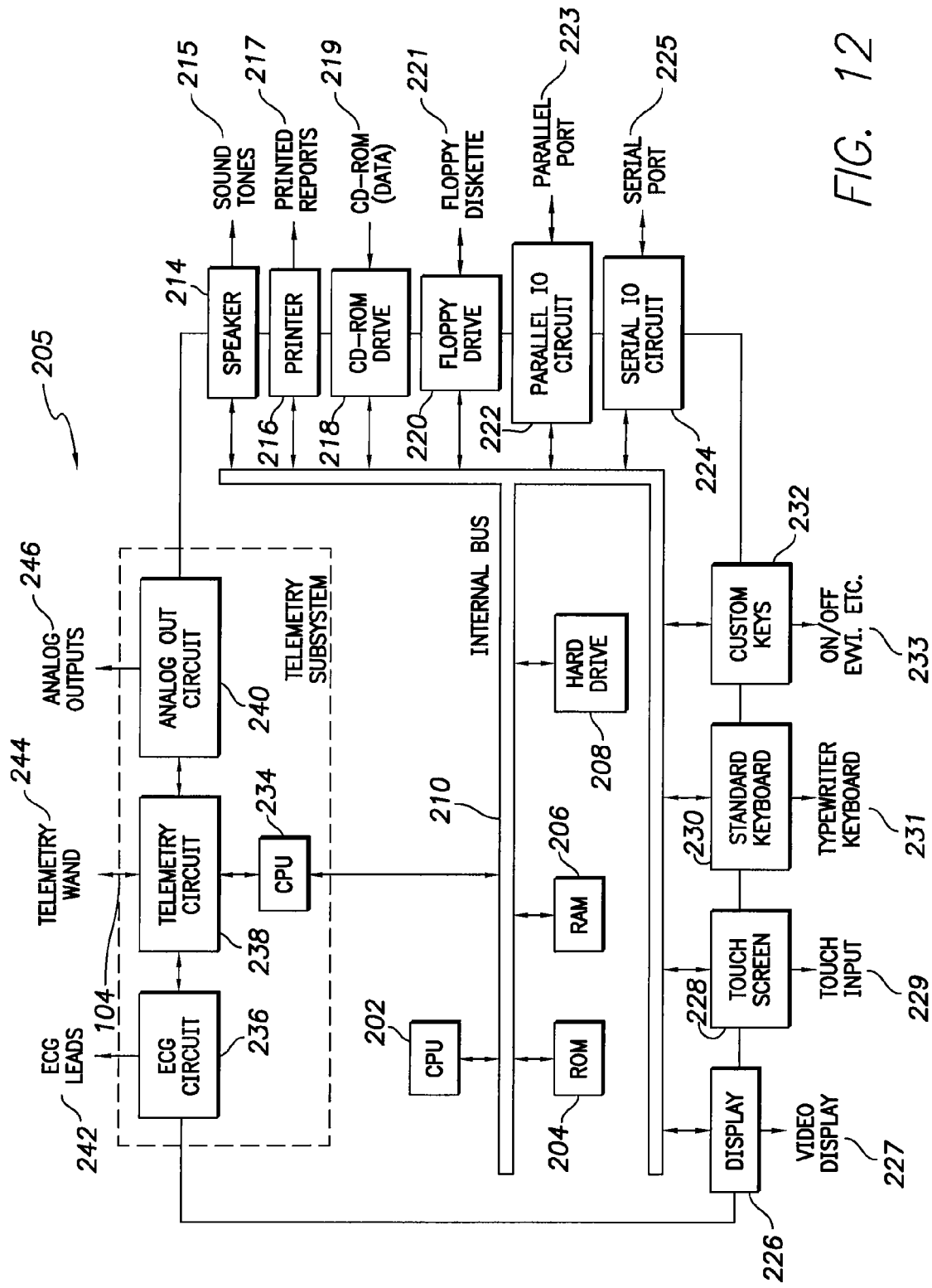
FIG. 12 illustrates a functional block diagram of certain components of an external programmer used to communicate with the implantable medical device shown in FIG. 1 utilized in accordance with an embodiment of the present invention.

FIG. 12 illustrates a functional block diagram of an external device 200, such as a programmer, that is operated by a physician or a health care worker to implement the processes of FIGS. 6 and 8 to determine STS variation trends as described above. The external device 200 interfaces with IMD 10 and may be utilized in a hospital setting, a physician's office, or even the patient's home to communicate with the IMD 10 to change a variety of operational parameters regarding the therapy provided by the IMD 10 as well as to select among physiological parameters to be monitored and recorded by the IMD 10. Further, the external device 200 may be utilized to interrogate the IMD 10 to determine the condition of a patient, to adjust the physiological parameters monitored, or to adapt the therapy to a more efficacious one in a non-invasive manner. Optionally, the operation of the processes of FIGS. 6 and 8 may be divided between the IMD 10 and the external device 200.

External device 200 includes an internal bus 210 that connects/interfaces with a Central Processing Unit (CPU) 202, ROM 204, RAM 206, a hard drive 208, a speaker 214, a printer 216, a CD-ROM drive 218, a floppy drive 220, a parallel I/O circuit 222, a serial I/O circuit 224, a display 226, a touch screen 228, a standard keyboard connection 230, a custom keys 232, and a telemetry subsystem 212. The internal bus 210 is an address/data bus that transfers information (e.g. either memory data or a memory address from which data will be either stored or retrieved) between the various components described. The hard drive 208 may store operational programs as well as data, such as reference ST segments, ST thresholds, timing information and the like.

The CPU 202 typically includes a microprocessor, a micro-controller, or equivalent control circuitry, designed specifically for controlling interfacing the external device 200 with the IMD 10. The CPU 202 may further include RAM or ROM memory, logic and timing circuitry, state machine circuitry, and I/O circuitry to interface with the IMD 10. Typically, the microcontroller 60 includes the ability to process or monitor input signals (data) as controlled by program code stored in memory (e.g., ROM 206).

In order for a physician or health care worker to communicate with the external device 200, a display 226, a touch screen 228, a standard keyboard 230, and custom keys 232 are provided. The display 226 (e.g., may be connected to a video display 227) and the touch screen 228 display text, alphanumeric information, data and graphic information via a series of menu choices to be selected by the user relating to the IMD 10, such as for example, status information, operating parameters, therapy parameters, patient status, access settings, software programming version, ST segment thresholds, and the like. The touch screen 228 accepts a user's touch input 229 when selections are made. The keyboard 230 (e.g., a typewriter keyboard 231) allows the user to enter data to the displayed fields, operational parameters, therapy parameters, as well as interface with the telemetry subsystem 212.

Furthermore, custom keys 232 turn on/off 233 (e.g., EVVI) the external device 200, a printer 216 prints hard-copies of any reports 217 for a physician/healthcare worker to review or to be placed in a patient file, and speaker 214 provides an audible warning (e.g. sounds and tones 215) to the user in the event a patient has any abnormal physiological condition occur while the external device 200 is being used. In addition, the external device 200 includes a parallel I/O circuit 222 to interface with a parallel port 223, a serial I/O circuit 224 to interface with a serial port 225, a floppy drive 220 to accept floppy diskettes 221, and a CD-ROM drive 218 that accepts CD ROMs 219.

The telemetry subsystem 212 includes a central processing unit (CPU) 234 in electrical communication with a telemetry circuit 238, which communicates with both an ECG circuit 236 and an analog out circuit 240. The ECG circuit 236 is connected to ECG leads 242, the telemetry circuit 238 is connected to a telemetry wand 244, and the analog out circuit 212 includes communication circuits, such as a transmitting antenna, modulation and demodulation stages (not shown), as well as transmitting and receiving stages (not shown) to communicate with analog outputs 246. The external device 200 may wirelessly communicate with the IMD 10 and utilize protocols, such as Bluetooth, GSM, infrared wireless LANs, HIPERLAN, 3G, satellite, as well as circuit and packet data protocols, and the like. The wireless RF link utilizes a carrier signal that is selected to be safe for physiologic transmission through a human being and is below the frequencies associated with wireless radio frequency transmission. Alternatively, a hard-wired connection may be used to connect the external device 200 to IMD 10, e.g., an electrical cable having a USB connection.

Figure 13:
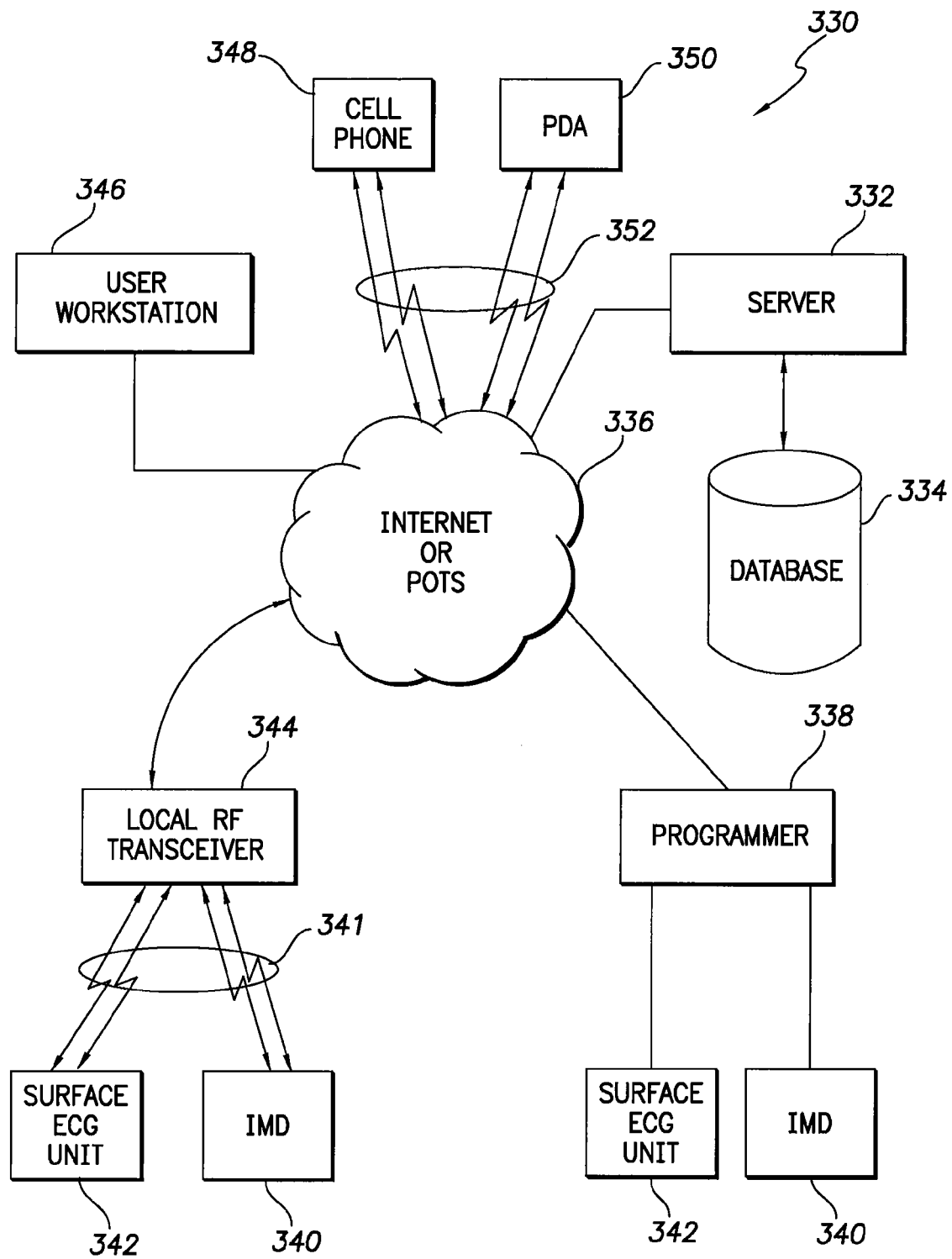
FIG. 13 illustrates a functional block diagram of a distributed processing system in accordance with an embodiment of the present invention.

FIG. 13 illustrates a distributed processing system 330 in accordance with an embodiment of this invention. The distributed processing system 330 includes a server 332 that is connected to a database 334, a programmer 338 (e.g. similar to external device 200 described above), a local RF transceiver 334 and a user workstation 346 electrically connected to a communication system 336 such as the internet, a voice over IP (VoIP) gateway, or a local plain old telephone service (POTS) such as a public switched telephone network (PSTN). Alternatively, the communication system 336 may be a local area network (LAN), a campus area network (CAN), a metropolitan area network (MAN), or a wide area network (WAM). The communication system 336 serves to provide a network that facilitates the transfer/receipt of cardiac signals, processed cardiac signals, histograms, trend analysis and patient status, and the like.

The server 332 is a computer system that provides services to other computing systems (e.g., clients) over a computer network. The server 332 acts to control the transmission and reception of information (e.g., cardiac signals, processed cardiac signals, ST segments, histograms, statistical analysis, trend lines, and the like). The server 332 interfaces with a communication system 336, such as the internet or a local POTS based telephone system, to transfer information between the programmer 338, the local RF transceiver 344, the user workstation as well as a cell phone 348, and a personal data assistant (PDA) 350 to the database 334 for storage/retrieval of records of information. For instance, the server 332 may download to a cell phone 348 or PDA 350 the results of processed cardiac signals, ST segment trends, or a patient's physiological state (e.g. is the patient having or has had an ischemia) based on previously recorded cardiac information. On the other hand, the server 332 may upload raw cardiac signals (e.g., unprocessed cardiac data) from surface ECG unit 342 or IMD 340 via the local RF transceiver 344 or the programmer 338.

Database 334 is any commercially available database that stores information in a record format in electronic memory. The database 334 stores information such as raw cardiac data, processed cardiac signals, statistical calculations (e.g., averages, modes, standard deviations), histograms, cardiac trends (e.g., STS trends), and the like. The information is downloaded into the database 334 via the server 332 or, alternatively, the information is uploaded to the server from the database 334.

The programmer 338 is similar to the programmer 200 described above and may reside in a patient's home, a hospital, or a physician's office. Programmer 338 interfaces with a surface ECG unit 342 and an IMD 340 (e.g., similar to ICD 10 described above). The programmer 338 may wirelessly communicate with the IMD 340 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 338 to IMD 10, e.g., an electrical cable having a USB connection. The programmer 338 is able to acquire cardiac signals from the surface of a person (e.g., ECGs), or the programmer is able to acquire intra-cardiac electrogram (e.g., IEGM) from IMD 340. The programmer 338 interfaces with the communication system 336, either via the internet or via POTS, to upload the cardiac data acquired from the surface ECG unit 342 or the IMD 340 to the server 332. The programmer 338 may upload more than just raw cardiac data. For instance, the programmer 338 may upload status information, operating parameters, therapy parameters, patient status, access settings, software programming version, ST segment thresholds, and the like.

The local RF transceiver 334 interfaces with the communication system 336, either via the internet or via POTS, to upload cardiac data acquired from the surface ECG unit 342 or the IMD 340 to the server 332. In one embodiment, the surface ECG unit 342 and the IMD 340 have a bi-directional connection with the local RF transceiver via a wireless connection 341. The local RF transceiver 344 is able to acquire cardiac signals from the surface of a person (e.g., ECGs), or acquire intra-cardiac electrogram (e.g., IEGM) from IMD 340. On the other hand, the local RF transceiver 344 may download stored cardiac data from database 334 or the analysis of cardiac signals from database 334 (e.g., ST segment statistical analysis, ST segment trends, and the like) information to the surface ECG unit 342 or IMD 340.

The user workstation 346 may interface with the communication system 336 via the internet or POTS to download information via the server 332 from the database 334. Alternatively, the user workstation may download raw data from the surface ECG unit 342 or IMD 340 via either the programmer 338 or the local RF transceiver 344. Once the user workstation 346 has downloaded the cardiac information (e.g., raw cardiac signals, ST segments, and the like), the user workstation 346 may process the cardiac signals, create histograms, calculate statistical parameters, or determine cardiac trends and determine if the patient is suffering from ischemia or another physiological condition. Once the user workstation 346 has finished performing its calculations, the user workstation 346 may either download the results to the cell phone 348, the PDA 350, the local RF transceiver 344, the programmer 338, or to the server 332 to be stored on the database 334.

In accordance with certain embodiments, methods and systems are provided that are able to measure STS variations over time are presented as STS trends. The STS trends are presented to physicians in a manner that is insightful to potential monitored changes in ischemic events. For example, the STS trends may be presented as graphs that depict the changes in STS variations over a period of time of various statistical parameters.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method for characterizing ST segment (STS) variations of a patient, comprising:
    collecting and storing STS variations for multiple data collection periods, each of the data collection periods separated by a cycle;
    calculating multiple statistical parameters based on the STS variations collected, wherein each statistical parameter is associated with a corresponding data collection period;
    sorting the calculated statistical parameters for the STS variations into a plurality of heart rate bins based on at least two or more of a normal resting heart rate bin, a normal active heart rate bin, an elevated heart rate bin, a fast heart rate bin, an arrhythmic heart rate bin, and a bradycardia heart rate bin for each of the multiple data collection periods; and
    constructing a STS variation trend of the sorted STS variations as a function of the sorted heart rate bins for each of the multiple data collection periods.

2. The method according to claim 1, wherein statistical parameters comprise at least one of an average, an average deviation, a standard deviation, a regression analysis, and combinations thereof.

3. The method according to claim 1 wherein statistical parameters comprises regression analysis comprises at least one of a simple linear regression, a least squares linear regression, a robust regression, a multiple linear regression, a non-linear regression, a maximum likelihood estimation, and combinations thereof.

4. The method according to claim 1, wherein the data collection period comprises at least of a one day period, a three day period, a seven day period, a ten day period and a fourteen day period.

5. The method according to claim 1, wherein start times for successive data collection periods are separated by a cycle, the cycle being based on a period of time elapsed since implant of an implantable medical device.

6. The method according to claim 1, further comprising presenting to a user as at least one of a display, a pictorial representation, a symbolic representation, a graph, a bar graph, a chart, a histogram, a pie chart, a Venn diagram, and combinations thereof.

7. The method according to claim 1, wherein the STS variation trend indicates an abnormal physiology.

8. The method according to claim 7, wherein the abnormal physiology comprises at least one of an ischemia, a myocardial infarction, a post-myocardial infarction, a silent myocardial infarct, an arrhythmia, a fibrillation, a heart block or a congestive heart failure.

9. A system for characterizing ST segment (STS) variations of a patient, comprising:
a memory module to store a plurality of cardiac signals having ST segments collected during multiple data collection periods, each of the data collection periods separated by a cycle, the memory module storing the values of STS variations; and
a processor module configured to:
calculate multiple statistical parameters based on the STS variations recorded,
sort the calculated statistical parameters for the STS variations into a plurality of heart rate bins based on at least two or more of a normal resting heart rate, a normal active heart rate, an elevated heart rate, a fast heart rate, an arrhythmic heart rate, and a bradycardia heart rate for each of the multiple data collection periods; and
construct a STS variation trend of the sorted STS variations as a function of the sorted heart rate bins for each of the multiple data collection periods.

10. The system of claim 9, wherein start times for successive data collection periods are separated by a cycle, the cycle being based on a period of time elapsed since implant of an implantable medical device.

11. The system of claim 9, wherein the memory module is configured to store STS variation data, statistical parameters, and STS trends.

12. The system of claim 11, wherein the memory module is configured to store the STS variation values and corresponding heart rates for each STS variation.

13. The system of claim 11, wherein the memory module is configured to store at least one of an average, an average deviation, a standard deviation, a regression analysis, a simple linear regression, a least squares linear regression, a robust regression, a multiple linear regression, a nonlinear regression, a maximum likelihood estimation and combinations thereof.

14. The system of claim 9, wherein the processor module comprises a statistical analysis module and a ST segment (STS) trend analysis module.

15. The system of claim 9, wherein the statistical parameter comprises at least one of an average, an average deviation, a standard deviation, a regression analysis, a simple linear regression, a least squares linear regression, a robust regression, a multiple linear regression, a nonlinear regression, and a maximum likelihood estimation.

16. The system of claim 9, further comprises a display that interfaces with the processor module to present to a user the STS trend to indicate whether a patient has an abnormal physiological condition.

17. The system of claim 9, wherein the data collection period comprises at least of a one day period, a three day period, a seven day period, a ten day period, and a fourteen day period.

18. The system of claim 9, further comprises a detector module to acquire a plurality of cardiac signals having ST segments during a data collection period, each data collection period separated by a cycle.

* * * * *